United States Patent [19]

Bölsterli

[11] Patent Number: 4,567,908
[45] Date of Patent: Feb. 4, 1986

[54] DISCHARGE SYSTEM AND METHOD OF OPERATING SAME

[75] Inventor: Martin Bölsterli, Zürich, Switzerland

[73] Assignee: Contraves AG, Zürich, Switzerland

[21] Appl. No.: 610,311

[22] Filed: May 14, 1984

[30] Foreign Application Priority Data

May 31, 1983 [CH] Switzerland .......................... 2971/83

[51] Int. Cl.⁴ .............................................. B67D 5/40
[52] U.S. Cl. .......................................... 137/1; 137/205; 137/209; 137/312; 222/375
[58] Field of Search ................... 137/1, 567, 568, 569, 137/205, 209, 312; 222/375, 318

[56] References Cited

U.S. PATENT DOCUMENTS

| 3,129,717 | 4/1964 | Main | 222/318 X |
| 3,228,608 | 1/1966 | Simm | 222/318 X |
| 3,747,412 | 7/1973 | Jones | |
| 4,179,932 | 12/1979 | Ranger | |

FOREIGN PATENT DOCUMENTS

| 0002103 | 5/1979 | European Pat. Off. |
| 2218569 | 10/1973 | Fed. Rep. of Germany |
| 2271558 | 2/1974 | France |
| 2510749 | 7/1981 | France |
| 545989 | 12/1973 | Switzerland |

Primary Examiner—Alan Cohan
Attorney, Agent, or Firm—Werner W. Kleeman

[57] ABSTRACT

A discharge system for a tubing system in an apparatus for the selective transport of fluid volume quantities, for instance in a particle analyzer. Fluid is transported by means of a delivery pump from a first vessel through a transport conduit to a second vessel. Carry-over from one specimen to the next as well as foam, droplets and bubbles at the outlet or delivery nozzle are to be circumvented. A substantially T-shaped fitting is arranged in the transport conduit and its lateral branch leads through a valve to a collector vessel which is maintained under vacuum by a pump. After closing the valve and filling the first vessel, the delivery pump is operated. When a predetermined fluid volume has been attained in the second vessel, the valve is opened and a further pump operated whereupon the entire fluid quantity contained in the transport conduit and in the first vessel is drawn into the collector vessel: in particular, the fluid in the outlet nozzle and in the tubing system connected to such outlet nozzle is drawn or sucked back. When only air is taken in, the pumps can be turned off and the process can be repeated. The reverse suction at the outlet nozzle prevents the formation of foam, droplets and bubbles and the conduits of the tubing system are well drained.

4 Claims, 4 Drawing Figures

DISCHARGE SYSTEM AND METHOD OF OPERATING SAME

BACKGROUND OF THE INVENTION

The present invention broadly relates to tubing systems and, more specifically, pertains to a new and improved construction of a discharge system as well as to a method of operating such a discharge system.

Generally speaking, the discharge system and method of the present invention are intended for at least one tubing run or system or conduit line in an apparatus for the selective transport of fluid volume quantities from a first vessel to a second vessel. The inventive discharge system for a tubing system in an apparatus for the selective transport of fluid quantities from a first vessel to a second vessel comprises an outlet or delivery nozzle arranged in an upper portion of the second vessel, a transport conduit leading from a lower portion of the first vessel to the nozzle, means for transporting a fluid contained in the first vessel through the transport conduit toward the second vessel, a collector vessel, means for drawing fluid into the collector vessel, a suction conduit arranged at the collector vessel for drawing and conducting fluid into the collector vessel and a valve arranged in the transport conduit or in the suction conduit.

It is known, for instance from the Swiss Pat. No. 545,989, to provide a transport conduit in an apparatus of the previously mentioned type which leads from a lower portion of a first vessel to a delivery nozzle arranged above a second vessel. Means are also known, for instance from the same document, which are suited for the transport of a fluid contained in the first vessel through the transport conduit to the second vessel.

It is also known, for instance from the European Patent Publication No. 2103-A1, to provide a collector vessel for flushing purposes as well as means for drawing fluid into the collector vessel, a suction conduit for the fluid arranged at the collector vessel and a valve arranged in the suction conduit for inhibiting or permitting flow through the suction conduit.

The apparatus and method of the present invention are especially intended to be applied to systems employed in particle analyzers for the serial or sequential analysis of blood samples or specimens. Such systems serve to transport specimens prepared in a first vessel into the second vessel where such specimens are tested or analysed. After testing, all vessels and conduits of the tubing system must be flushed and fully discharged in order to avoid dilution errors and the entrainment or carry-over of specimen matter.

Simply blowing out the conduits in a system, as disclosed in the aforementioned Swiss Pat. No. 545,989, does not lead to the desired result in modern, complex particle analyzers in which erythrozytes as well as thrombozytes and leucozytes are tested. For testing leucozytes, the blood samples or specimens are treated by a haemolysator which influences the surface tension of the fluid such that the specimens tend to form foam, bubbles and droplets when mixed and when the conduits are blown out with air, especially in the proximity of the outlet or delivery nozzle. The foam can only be flushed out of the vessels with difficulty. Alternating tests or measurements of erythrozytes, on the one hand, and thrombozytes or leucozytes, on the other hand, are thus hampered or the flushing and discharge of the conduits becomes very complex.

The flushing of the conduits with a flushing solution by means of an apparatus known from the aforementioned European Patent Publication No. 2103-A1 does make it possible to largely eliminate the carry-over of specimens and the influence of the haemolysator but leaves the conduits full. When discharging these conduits by blowing them out, bubbles and droplets still form, especially at the outlet or delivery nozzle: at the end of the blowing out process, when the pressure and the air velocity subside, the fluid retained on the walls of the conduits by surface tension forces slowly flows back to the delivery nozzle and a bubble forms and remains suspended on such delivery nozzle. A few alternating fluid and air segments also form in the conduit as well as some foam when such segments reach the delivery nozzle.

SUMMARY OF THE INVENTION

Therefore, with the foregoing in mind, it is a primary object of the present invention to provide a new and improved construction of a discharge system and a method of operating the same which do not have associated with them the aforementioned drawbacks and shortcomings of the prior art constructions.

Another and more specific object of the present invention aims at providing a new and improved construction of a discharge system of the previously mentioned type and a method of operating the same which make possible the draining or discharge of vessels and transport conduits both before and after the transport of samples or specimens into the testing or measuring vessel and before and after flushing the vessels and the transport conduit without the formation of foam or droplets.

Yet another further significant object of the present invention aims at providing a new and improved construction of a discharge system of the character described which is relatively simple in construction and design, extremely economical to manufacture, highly reliable in operation, not readily subject to breakdown or malfunction and requires a minimum of maintenance and servicing.

Now in order to implement these and still further objects of the invention, which will become more readily apparent as the description proceeds the discharge system of the present invention is manifested by the features that it comprises a connection fitting having a through or continuous tube and a lateral branch tube, the through tube being arranged in the transport conduit and the lateral branch tube being connected to the suction conduit.

The method of the present invention is manifested by the features that it comprises the steps of establishing an initial state of the system to be discharged by closing the valve and filling the first vessel, operating the means for transporting the fluid from the first vessel to the second vessel, opening the valve upon obtaining a desired volume of fluid in the second vessel whereupon first fluid and then air are conducted to the collector vessel from the outlet or delivery nozzle, from the first vessel, from the transport conduit and from the suction conduit and, when only air is drawn into the collector vessel, terminating the operation of the means for transporting the fluid.

With this discharge system and this method, the beneficial result is obtained that no return flow fluid contaminates or adulterates the specimens or alters the dilution of the specimens since the transport conduit and the outlet or delivery nozzle are completely drained or discharged and the cleansing of the vessels is simpler and therefore less time-consuming.

BRIEF DESCRIPTION OF THE DRAWINGS

The invention will be better understood and objects other than those set forth above, will become apparent when consideration is given to the following detailed description thereof. Such description makes reference to the annexed drawings wherein throughout the various figures of the drawings there have been generally used the same reference characters to denote the same or analogous components and wherein.

DETAILED DESCRIPTION OF THE PREFERRED EMBODIMENTS

Figure 1:
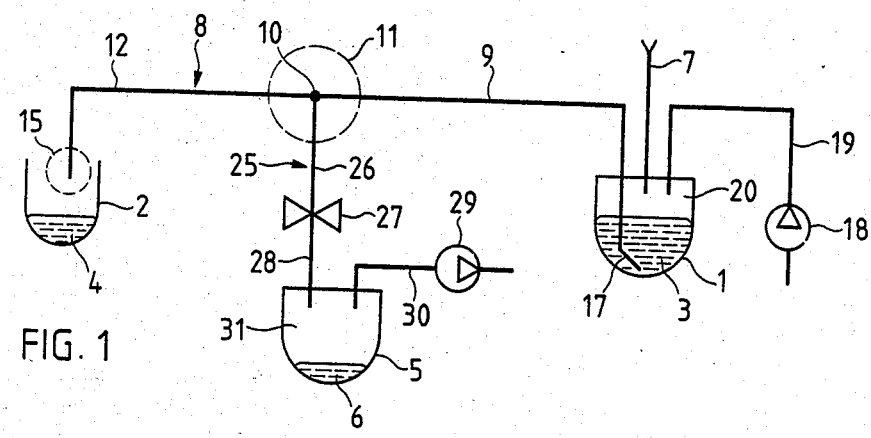
FIG. 1 schematically shows an apparatus of the previously mentioned type provided with the discharge system according to the invention.

Describing now the drawings, it is to be understood that to simplify the showing of the drawings, only enough of the structure of the discharge system and related apparatus has been illustrated therein as is needed to enable one skilled in the art to readily understand the underlying principles and concepts of this invention. The illustrated exemplary embodiment of the discharge system shown in FIG. 1 will be seen to comprise a first vessel 1 and a second vessel 2. A suitable fluid 3 is contained in the first vessel 1, a desired volume of which is to be transported into the second vessel 2. The already transported volume of fluid is designated with the reference numeral 4. When the fluid 4 reaches the desired volume, the remainder of the fluid 3 is to be removed or disposed of and the first vessel 1 is to be completely drained or discharged. A collector vessel 5 is provided for this purpose and is intended for the reception of the fluid to be removed. The fluid already accommodated in the collector vessel 5 is designated with the reference numeral 6. New fluid 3 can be filled into the first vessel 1 through the infeed conduit 7.

A transport conduit designated in its entirety with the reference numeral 8, serves for the transport of the fluid 3 from the first vessel 1 to the second vessel 2. A portion 9 of this transport conduit 8 leads from the first vessel 1 to a connector fitting which is designated in its entirety with the reference numeral 10 and is symbolically encompassed by the broken-line circle 11. Another portion 12 of the transport conduit 8 leads from the connector fitting 10 to the second vessel 2. The conduit portions 9 and 12 of the transport conduit 8 of the tubing system may comprise, for instance, a flexible tube or hose of inert plastic (polyvinylchloride, polyethylene or equivalent materials) having, for instance, an inside diameter of about 2 millimeters.

Figure 3:
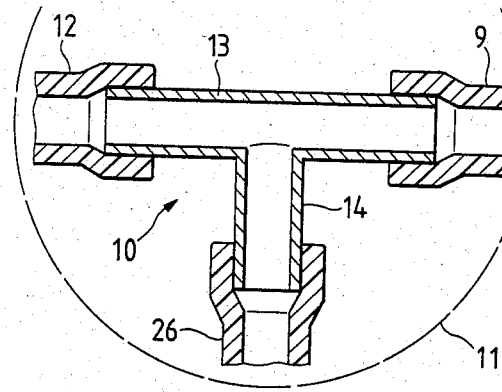
FIG. 3 schematically shows in section a connector fitting for the connection of the discharge system in the transport conduit of the apparatus constructions of FIGS. 1 and 2.

The connector fitting 10 will now be described in more detail in relation to FIG. 3. The components schematically or symbolically indicated within the circle 11 in FIG. 1 are represented in section within the larger scale circle 11 depicted in FIG. 3. The connector fitting 10 is substantially T-shaped and is formed with approximately equal legs or spigots in order to connect three similar tubes or hoses with one another. The connector fitting 10 comprises a through or continuous tube or body 13 and a lateral branch tube or leg 14 which are in mutual intercommunication and whose inside diameters are approximately the same as the inside diameter of the therewith connected tubing or hoses. It will be seen that the portions 9 and 12 of the transport conduit 8 are connected to the connector fitting 10 such that the transport conduit 8 leads through the connector fitting 10 or, respectively, the through tube or body 13 is arranged in the transport conduit 8. For this purpose an end of each of the tubing lines or hoses constituting the conduit portions 9 and 12 of the transport conduit 8 are fitted over respective ends of the through tube or body 13, as can be seen in FIG. 3.

Figure 4:
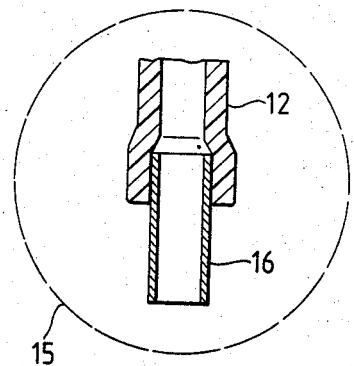
FIG. 4 schematically shows in section an outlet or delivery nozzle for transporting fluid into the second vessel.

The end of the conduit portion 12 of the transport conduit 8 remote from the connector fitting 10 is symbolically indicated within the broken-line circle 15 in FIG. 1 and will now be described in more detail in relation to FIG. 4. An outlet or delivery nozzle 16 formed from a stub of tubing or pipe of about the same inside diameter as the inside diameter of the therewith connected tubing or hose is provided at the end of the tubing or hose constituting the conduit portion 12 of the transport conduit 8. The corresponding end of the tubing or hose constituting the portion 12 of the transport conduit 8 is fitted on one end of the tube stub 16, as is shown in section in FIG. 4.

The connector fitting 10 and the outlet or delivery nozzle 16 may comprise rigid inert plastic or inert metal such as, for instance, stainless steel. The ends of these parts may be formed with ferrules or annular ribs or teeth for the better fitting and anchorage of the tubing or hoses in known manner. In one exemplary embodiment, the connector fitting 10 comprises transparent polyacetal while the outlet or delivery nozzle is made of thin-walled stainless steel (about 0.2 millimeter wall thickness).

As can be seen in FIG. 1, the outlet or delivery nozzle 16 is arranged in relation to the second vessel 2 such that it opens into the upper portion of this second vessel 2 but is not immersed in the fluid 4 at its highest level. The outlet or delivery nozzle 16 need not be arranged vertically, it can also deliver the fluid diagonally downward. The end 17 of the conduit portion 9 of the transport conduit 8 remote from the connector fitting 10 does, however, immerse in the fluid 3 down to the lowermost position in the lower portion of the first vessel 1. It is advantageous to form the end 17 of the conduit portion 9 as a separate tube upon which one end of the tubing or hose constituting the conduit portion 9 is fitted. The end 17 can thus be securely positioned at the lowest point of the first vessel 1 in order to enable the complete drainage or discharge of this first vessel 1.

In the embodiment according to FIG. 1, a delivery pump 18 is provided as a means for transporting or conveying the fluid 3 out of the first vessel 1 and through the transport conduit 8 in the direction of the second vessel 2. This pump 18 generates an air pressure of about 250 millibar (gauge) in a pressure conduit 19. The first vessel 1 is formed as a closed space or chamber 20 into the upper portion of which the conduits 19 and 7 open such that they do not immerse in the fluid 3.

Furthermore, the infeed conduit 7 is provided with a suitable valve or closure in a known and not particularly shown manner in order that the air entrained from the conduit 19 into the space 20 and its pressure may not escape through the infeed conduit 7. The fluid 3 is pressed or displaced into the transport conduit 8 and transported in the latter by the air pressure in the space or chamber 20. In this embodiment, it is particularly advantageous that the pump 18 need only generate air pressure, that is, it need not directly pump liquid.

Figure 2:
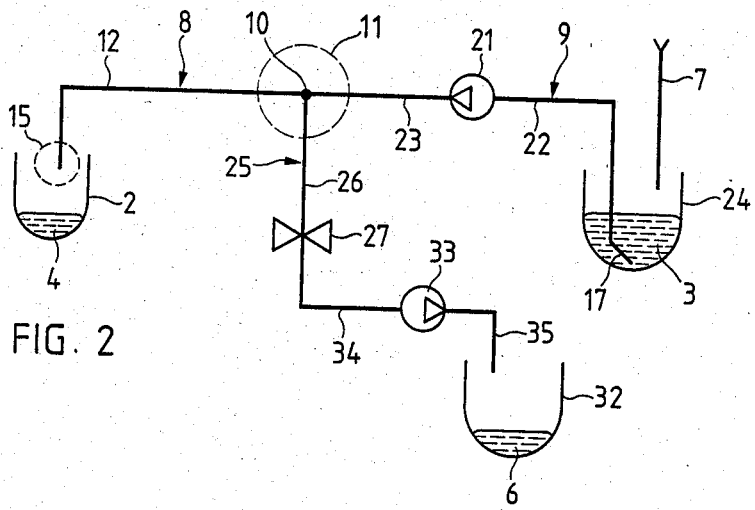
FIG. 2 schematically shows a further embodiment of the apparatus with a modified construction of discharge system according to the invention.

In the embodiment of FIG. 2, a delivery pump 21 is arranged in the conduit portion 9 of the transport conduit 8 as a means of transporting or conveying the fluid 3 from the first vessel 24 through the transport conduit 8 in the direction of the second vessel 2, that is, the conduit portion 9 of the transport conduit 8 is divided into two sub-portions 22 and 23 by the delivery pump 21. In this embodiment, the delivery pump 21 must be capable of transporting both liquid and air in the direction from portion 22 to portion 23 of the transport conduit 8; for instance, the pump 21 may be a squeezed hose pump of known type. A vacuum countering the fluid transport may not be allowed to form in the first vessel 24 during the operation of the pump 21. The first vessel 24 is therefore open to the atmosphere in this embodiment, as is shown in FIG. 2.

In both of the exemplary embodiments shown in FIGS. 1 and 2, the lateral branching or branch tube or leg 14 of the connector fitting 10 is connected to a suction conduit designated in its entirety with the reference numeral 25. A portion 26 of this suction conduit 25 consists, as do the conduit portions 9 and 12 of the transport conduit 8, of a tubing member or hose, one end of which is fitted to the lateral branching or branch tube or leg 14 of the connector fitting 10 such that the inside diameter remains about the same throughout. A valve 27 is arranged at the other end of the portion 26 of the suction conduit 25 and can selectively close or open the suction conduit 25.

In the embodiment according to FIG. 1, another portion 28 of the suction conduit 25 leads from the valve 27 to the collector vessel 5. In this embodiment, a pump 29 is provided as a means for drawing the fluid 6 into the collector vessel 5 and generating a vacuum of about 250 millibar in a suction conduit 30. The collector vessel 5 is constructed as a closed space or chamber 31 into the upper portion of which the suction conduit 30 and the portion 28 of the suction conduit 25 open such that they do not immerse in the fluid. Fluid is drawn into the collector vessel 5 from the connector fitting 10 by the vacuum in the space or chamber 31 when the valve 27 is open. In this embodiment, it is particularly advantageous that the pump 29 need only draw air, that is, need not pump liquid. The pumps 18 and 29 can therefore be of the same type and serve as conveying means for the fluid.

In the embodiment of FIG. 2, a pump 33 is arranged in the suction conduit 25 between the valve 27 and the collector vessel 32 as a means for drawing the fluid 6 into a collector vessel 32, that is, a portion 34 of the suction conduit 25 leads from the valve 27 to the pump 33 and a portion 35 of the suction conduit 25 leads from the pump 33 to the collector vessel 32. In this embodiment, the pump 33 must be capable of transporting both liquid and air in the direction from portion 34 to portion 35 of the suction conduit 25; for instance, the pump 33 may be a squeezed hose pump of known type. A pressure in excess of atmospheric pressure countering the suction action may not be allowed to form in the collector vessel 32 during the operation of the pump 33. The collector vessel 32 is therefore, in this embodiment, open to the atmosphere, as is shown in FIG. 2.

In both of the embodiments of the discharge system described, it is possible to drain or discharge the transport conduit 8, comprising conduit portions 9 and 12 as well as the through tube or body 13 of the connector fitting 10, and also the lateral branching or branch tube or leg 14 of the connector fitting 10 in an apparatus for the transport of fluid volume quantities from a vessel 1 or 24 to a vessel 2 via such transport conduit 8, without the formation of bubbles, droplets or foam. To this end, the discharge system is operated in the manner to be described below, that is, according to the following sequential steps.

a. Establishment of an initial state: the valve 27 is closed and the first vessel 1 or 24 is adequately filled to hold a greater quantity of fluid 3 than the desired fluid volume quantity 4 to be transported into the second vessel 2. In the embodiment according to FIG. 1, the space 20 and the vessel 1 are initially under atmospheric pressure. The suction pump 29 or 33 is in operation; in the embodiment according to FIG. 1, the space 31 and the vessel 5 are under vacuum.

b. The pump 18 or 21 is operated in order to transport fluid from the first vessel 1 or 24 to the second vessel 2. The transport conduit 8 fills with fluid and the fluid flows through this transport conduit.

c. When the predetermined desired fluid volume or fluid volume quantity has been filled into the second vessel 2, further filling is terminated. To this end, the valve 27 is opened. The fluid at the connector fitting 10 is immediately drawn into the lateral branching or branch tube or leg 14 instead of continuing to flow from the conduit portion 9 into the conduit portion 12 of the transport conduit 8.

It will be understood that to obtain this result the vacuum level in the portion 26 of the suction conduit 25 must be greater than the delivery capacity in portion 9 of the transport conduit 8. In the embodiment with two pumps of approximately equal capacity according to FIG. 1, the lengths of the conduits are sized such that a greater pressure gradient arises between the end 17 of the conduit portion 9 of the transport conduit 8 and the connector fitting 10 than between the connector fitting 10 and the end of portion 28 of the suction conduit 25 located in the space 31 for a constant volume rate of flow. Then the conduit portion 26 at the connector fitting 10 is under vacuum with respect to the conduit portion 9. In the embodiment according to FIG. 2, the pumps 21 and 33 are sized such that the delivery capacity of the pump 33 is greater than the delivery capacity of the pump 21. Then the conduit portion 26 at the connector fitting 10 is under vacuum with respect to the conduit portion 23.

In both embodiments the fluid flowing from the conduit portion 9 or 23 is fully accommodated by the conduit portion 26. The vacuum or underpressure in the conduit portion 26 also assures that the fluid contained in the conduit portion 12—that is, in the tubing member or hose 12 and in the outlet or delivery nozzle 16—is drawn or sucked back in the direction of the connector fitting 10. The process continues until the vessel 1 or 24 and the transport conduit 8 are drained or discharged. Neither foam nor droplets or bubbles can form on the outlet or delivery nozzle 16 since the fluid is not discharged through the nozzle. At the termination of this procedure, only air can come through the suction conduit 25 into the collector vessel 5 or 32.

d. When only air is taken in through the suction conduit 25 into the collector vessel 5 or 32, the operation of the pump 18 or 21 is terminated.

Subsequently, method step "a" can be performed again: the methods steps a, b, c and d can be recurrently sequentially repeated. The discharge system described in the apparatus disclosed is, for example, employable in a particle analyzer for precisely filling the second vessel 2 with specimen fluid on the one hand, or, on the other hand, in order to discharge or drain the transport conduit 8 in all its conduit runs or portions after testing or measurement—more specifically after each flushing—such that no residue remains which could be entrained or carried over with a next charge of fluid and such that neither foam nor droplets on bubbles can detrimentally influence the precision of the volume measurement or of the dilution of fluid.

It will be understood that, in relation to the connector fitting 10, the T-shaped embodiment described and illustrated in FIG. 3 with a through tube or body 13 and a lateral branch tube or leg 14 arranged perpendicularly thereto is preferred primarily on the grounds of cost and fabrication advantages but is only one of several possible embodiments. The connector fitting 10 could as well be star-shaped or Y-shaped with three connection legs or spigots, the through tube then being considered to be angled or bent in its middle region and to comprise two connection tubes or spigots. The construction of such a star-shaped or Y-shaped embodiment is then obvious when considered in relation to FIG. 3, so that a further illustration of this embodiment is not necessary.

While there are shown and described present preferred embodiments of the invention, it is to be distinctly understood that the invention is not limited thereto, but may be otherwise variously embodied and practiced within the scope of the following claims. Accordingly,

What I claim is:

1. A discharge system for a tubing system in an apparatus for the selective transport of fluid quantities from a first vessel to a second vessel, comprising:
    a transport conduit for flow communicating the first vessel with the second vessel;
    a delivery nozzle arranged in an upper portion of the second vessel;
    said transport conduit leading from a lower portion of the first vessel to said delivery nozzle;
    means for transporting a fluid contained in the first vessel through the transport conduit in the direction of the second vessel;
    a third vessel defining a collector vessel cooperating with the transport conduit;
    pump means for drawing fluid into said collector vessel;
    a suction conduit cooperating with said fluid drawing pump means and said collector vessel for drawing and conducting fluid into the collector vessel;
    a valve arranged in said suction conduit;
    a connection tee fitting having a through tube and a lateral branch tube;
    said through tube being arranged in the transport conduit; and
    said lateral branch tube being connected to the suction conduit.

2. A method for discharging a tubing system in an apparatus for the selective transport of fluid quantities from a first vessel to a second vessel by means of a discharge system comprising a delivery nozzle arranged in the second vessel, a transport conduit leading from the first vessel to the delivery nozzle, means for transporting a fluid contained in the first vessel through the transport conduit in the direction of the second vessel, a collector vessel, means for drawing fluid into the collector vessel, a suction conduit cooperating with the collector vessel for drawing and conducting fluid into the collector vessel, a valve arranged in the suction conduit, a connection fitting having a through tube arranged in the transport conduit and a lateral branch tube connected to the suction conduit, comprising the recurrent sequence of steps of:
    establishing an initial state of the tubing system by closing said valve and filling the first vessel;
    operating the means for transporting the fluid from the first vessel to the second vessel;
    upon obtaining a desired volume of fluid in the second vessel opening the valve, whereupon at first fluid and later air are drawn into said collector vessel from said delivery nozzle, from said first vessel, from said transport conduit and from said suction conduit; and
    terminating the operation of the means for transporting the fluid when only air is drawn into the collector vessel.

3. The method as defined in claim 2, wherein:
    said initial state of the tubing system is established while the fluid drawing means is operative.

4. The method as defined in claim 2, wherein:
    said initial state of the tubing system is established before the fluid drawing means is operative; and
    placing into operation said fluid drawing means at least prior to obtaining said desired volume of fluid in the second vessel.

* * * * *